United States Patent [19]

Donnerhack et al.

[11] Patent Number: 4,841,969
[45] Date of Patent: Jun. 27, 1989

[54] DEVICE FOR THE PRODUCTION OF A COLD TREATMENT-GAS FOR CRYOTHERAPY

[75] Inventors: Andreas Donnerhack, Krefeld; Kurt P. Schneider, Nettertal, both of Fed. Rep. of Germany

[73] Assignee: Messer Griesheim GmbH, Frankfurt am Main, Fed. Rep. of Germany

[21] Appl. No.: 56,112

[22] Filed: Jun. 1, 1987

[30] Foreign Application Priority Data

Jun. 25, 1986 [DE] Fed. Rep. of Germany ....... 3621425

[51] Int. Cl.$^4$ ..................... A61F 7/00; B65D 90/04; F16C 7/02
[52] U.S. Cl. .................................. 128/400; 220/901; 128/DIG. 27; 62/50.1
[58] Field of Search ............ 128/DIG. 27, 400, 303.1, 128/399; 62/45, 50, 52, 55.5, 457; 220/901

[56] References Cited

U.S. PATENT DOCUMENTS

| 3,199,303 | 8/1965 | Haamamm et al. ........ 128/DIG. 27 |
| 3,628,347 | 12/1971 | Packett ..................................... 62/50 |
| 4,163,371 | 8/1979 | Groninger ............................... 62/50 |
| 4,299,091 | 11/1981 | Carter et al. ............................. 62/50 |
| 4,693,252 | 9/1987 | Thoma et al. ....................... 128/400 |

FOREIGN PATENT DOCUMENTS

| 0175047 | 3/1986 | European Pat. Off. .... 128/DIG. 27 |
| 2603852 | 8/1978 | Fed. Rep. of Germany .......... 62/50 |
| 2070434 | 9/1981 | United Kingdom ....... 128/DIG. 27 |

Primary Examiner—Richard C. Pinkham
Assistant Examiner—Mark S. Graham
Attorney, Agent, or Firm—Connolly & Hutz

[57] ABSTRACT

A device for producing cyrotherapy with liquid nitrogen includes a container for the liquid nitrogen with electrical heating in its interior. The container has a maximum volume of 50 l and the electrical heating is a heating element comprising a self-regulating strip heater secured in the interior of the container.

4 Claims, 1 Drawing Sheet

DEVICE FOR THE PRODUCTION OF A COLD TREATMENT-GAS FOR CRYOTHERAPY

BACKGROUND OF INVENTION

Devices for conducting cryotherapy by means of a cold treatment-gas produced from liquid nitrogen are already well-known. In medical practice up to now, exclusively expensive devices have been the rule. These qualify indeed for the requisite high standards of clinics or in the larger practices. For those doctors, however, who make use of cryotherapy in the cases of only a few of their patients, the high investment costs in the introduction of such devices which produce a cold blast has long been a deterrent factor. Thus, in the area of established private practice, there has existed a need for a simplified cold-blast device by which the well-known and traditional expenses entained in the treatment could be reduced dramatically. This applies as well also to individual patients themselves, who carry out cryotherapy on themselves at home. It is a known fact that patients treat themselves after having received due diagnosis and instructions from their doctor regarding cryotherapy. The application of cold packs is likewise no problem for the patient, with careful following of instructions. Since these cold pack refrigerants are usable continuously over a long period, self-treatment in such cases makes sense and is even desirable. The identical pre-conditions for marginal requirements exist and apply also for treating oneself with cold-treatment gas. However, there is no suitable apparatus available for self-treatment.

A therapy device which would be put to use in both of the above areas would have to meet two requirements. First of all, investment costs for it should lie within a range that would be tolerable for a private individual. Secondly, there should not arise any risk for the consumer that would result from the simplification of the device. This is so, namely, because, in the area of the individual's treating himself, the fact must be taken into account that, by and large, he will be a layman in both the technical and the medical sense. The task which lies at the heart of the invention is, therefore, to create a device for the production of a cold-treatment gas from liquid nitrogen for the purposes of cryotherapy that would be conceived for only occasional application and thus would be simple in construction, economical to manufacture, and uncomplicated to use; at the same time, however, entirely without any risk for the consumer.

SUMMARY OF INVENTION

An object of this invention is to provide a device which meets the above needs. In accordance with the invention a heating element is utilized which is built compactly into the liquid nitrogen container. This heating element is constructed as an auto-regulative strip heater and may be installed at the bottom of the container in a spiralling configuration by means of clamps. The supply line may likewise be conducted up and out through the neck of the container by the appropriate clamps situated on the interior walls of the container. Such a heating element may be secured, in the manner mentioned, prior to the final construction of the container, without hindering any of the other work in progress on the container assembly. Prior art devices have used heating elements which must be removed when the container is being filled. One well-known system operates with a heating element that is built permanently in the liquid nitrogen container. However, in such a case there is need for a widenecked container specially made for the occasion. The advantage of the device according to the invention consists therein that it embodies the idea of a standard-type container on the one hand, while on the other, the very small rate of vaporization associated with narrow-necked containers may be resorted to in spite of the compact construction of the heating system.

Essential to the realization of the intended simplicity is the design of the heating element as a self-regulating strip heater.

In order to prevent damaging the heating element or the container after the liquid nitrogen in the container has been consumed, it was always necessary in the case of the previously well-known systems to equip them with expensive temperature or heat-flow regulating devices. The employing of a self-regulating strip heater renders these devices superfluous. These heating cables are obtainable as ordinary merchandise. The fact is of significance for the device according to the invention that, without external influence of the supply of current, the heating power drops, and the temperature will not exceed a certain limit. By a correct dimensioning of the self-regulating strip heater, the maximal temperature limit can be so determined that, when the nitrogen has been depleted, neither the container nor the heating element will be damaged. The self-regulating strip heater is provided with an insulation layer made of plastic, which exhibits high rupture resistance at very low temperatures. Thus, this insulating layer is not impaired mechanically in its intended role in the liquid nitrogen container. In addition, the plastic layer forms a protection against moisture entering the feed line. Thus, the humidity that is to be expected always in conjunction with lower temperatures will not cause any difficulties for the electrical safety of the system.

Taking into account the precise and purposeful use to which it will be put, the volume of the container will be limited to a maximum of 50 liters. The device according to the invention may therefore be constructed with a view to conservation of space. On the other hand, it may be made use of for several weeks with just one filling.

As a container for liquid nitrogen, a standard vessel with a small flange may be used which is, as a rule, equipped with safety valve and manometer. For its being put into service in accordance with the invention, it needs to be pressurized during construction, because of heat introduction, only to the extent that the resultant cold gas must be discharged from the open end of the vessel. Thus, there is no need for a manometer. Instead of it, the feed line of the heating cable will exit through the provisional lateral opening on the neck. As feed or supply able, ordinary electric cables may be employed, the insulatory layers of which will consist of cold-resistant plastic. These supply lines are likewise so mounted that they cannot be shifted. Thus, any mechanical demand placed on them in their cold state will not take place. The safety valve is to be retained on the container, in order for the system to be protected against any undesired pressure buildup resulting from a negligent or unintentional closing of the exhaust orifice.

In the system just described, the actual neck opening in the area of the flange is completely separate from the heating apparatus. The installment of the treatment hose is therefore made essentially more simple, in comparison with the usual well-known devices, because, whenever a dismantling is necessary in order to fill the container, it is only the treatment hose, not the heating element, that needs to be removed.

The cooling of the external hose surfaces must be avoided, not for its length of service, but only for a single treatment, which as a rule does not last for more than 2 to 3 minutes. Therefore, there is no necessity for lining the hose with expensive insulation. It has proven to be sufficient to insulate the actual refrigerant-conductive spiral hose of PVC simply with a layer of plastic foil and one of foil-layered felt. This is then covered completely with a plastic corrugated hose.

In the device according to the invention, any regulation of temperature of the refrigerant gas is waived. Because of heating with constant current, a constant stream of cold gas will result during the operation which, after a brief time of flow, produces a constant refrigerant gas temperature at the nozzle of the hose.

Given all the conditions which have been mentioned, it is also true that the electrical guidance of the apparatus is considerably simplified, in comparison with previously known systems. The strip heater may be connected to the system voltage directly. In order to meet the requisite safety criteria, it is necessary only to hook up a main switch and a safety element into this circuit.

In addition, this circuit may be provided with a time-control unit which will allow advance choice of treatment durations for every use. When the clock runs out, the apparatus will automatically shut itself off. This time-control unit is of course not absolutely necessary for operating the therapy device; however, it increases the convenience index without obstructing in any way the object of the invention, namely, to present a commendable device.

The various electrical installation elements described may be secured within a small casing located on the neck of the container, but without interfering with the dismantling of the treatment hose, or the filling of the container through the neck orifice.

THE DRAWINGS

FIG. 1 is a cut-away side view of the container with heating element in accordance with this invention; and FIG. 2 is an exploded view of the neck of the container shown in FIG. 1.

DETAILED DESCRIPTION

Figure 1:
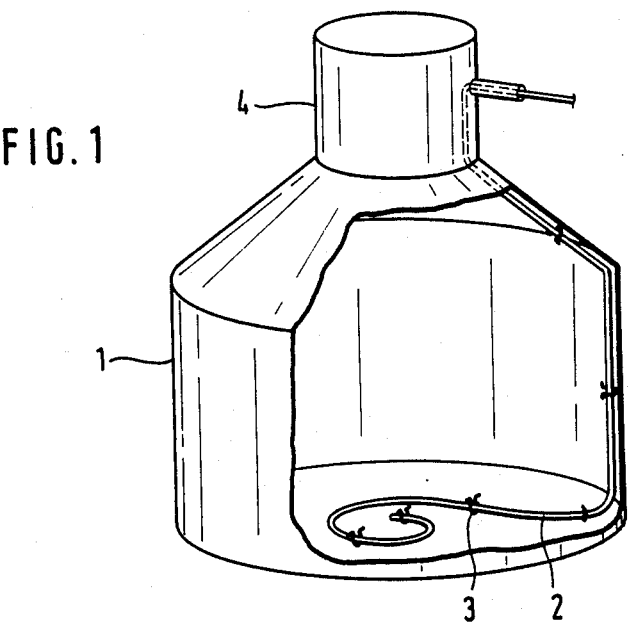

The container 1 represented in FIG. 1 is a standard vessel, designed with a narrow neck, with 30 l contents space. The details of insulation and the double-walled design are not presented. Corresponding to the invention, there is a self-regulating strip heater 2 at the bottom and on the internal wall of the container, solidly installed with the expedient of clamps 3, and drawn up to the outside by way of the neck 4 of the container.

Figure 2:
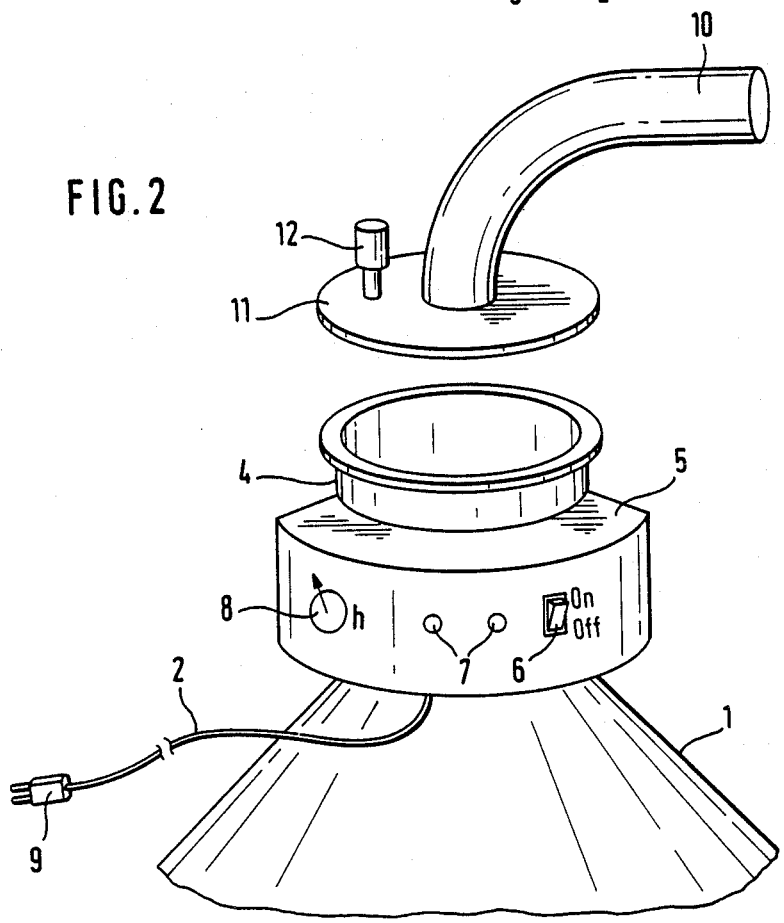

FIG. 2 shows the neck of the container in detail. A small casing 5 is secured to it, in which the main switch, or control switch 6, fuses 7, and a time-control unit or clock, 8, are arranged. As soon as the plug 9 is connected to the electrical circuit, the device is ready for operation. After activation of the time-control unit 8, cold treatment-gas is produced for the duration corresponding to the time selected, which is conducted to the place of treatment by the hose 10. The hose 10 is fastened to the neck 4 of the container by means of the flange 11. Inside the flange 11, a safety valve 12 is arranged.

From the viewpoint of safety technology, the device of the invention satisfies the requirements which apply to cold-blast therapy. Even with continual use of the device, only very limited amounts of nitrogen are liberated, so that, under normal conditions, the oxygen content of the surrounding air in the room will not be reduced appreciably. The cold treatment-gas that is produced is dry. The escape of liquid nitrogen from the treatment hose is not possible. The employing of the device in the area of self-treatment is therefore entirely supportable.

The device of the invention may be produced with a fraction of the expense that is necessary for the currently known devices for conducting cryotherapy. The investment costs associated with it are obviously, for the patient, situated within a quantitative range which permits him to acquire the device without any assistance whatsoever from health insurance.

The costs of operation of the device may be estimated on the basis of statistical mean value for treatment sessions. On the assumption of an average duration of treatment of 2 minutes, and one of 2 treatments per day, the conclusion is that the liquid nitrogen use in this treatment and the auto-vaporization of 30 l of the container enjoy a duration period of the entire system of more than 3 weeks. The result is a practical re-servicing interval on the part of the refrigerant suppliers.

SUMMARY

Devices for producing a cold treatment-gas from liquid nitrogen for cryotherapy are well-known, and have been confirmed through their services in clinics and medical centers. Often, there is a cold mixture of nitrogen and atmospheric air produced as treatment gas. Because of installations for regulating mixture and temperature, humidity elimination and purity of the ambient air, these well-known devices are expensive and occupy comparatively large space.

A commendable small device for only occasional applications, as, for instance, use in the home, consists of a standard small container with a maximum volume content of 50 l, in the inside of which an electrical heating element comprised of a self-regulating strip heater 2 is mounted. Inside a casing 5 which is mounted on the neck 4 of the container 1, an electrical fuse 7, the control switch 6, and a time-control unit 8 may be arranged. See FIG. 2.

We claim:

1. In a device for the producing of a cold treatment-gas from liquid nitrogen, for cryotherapy, with an insulated container for storing the liquid nitrogen, and electrical heating arranged within the container interior, the improvement being said container being a small container with a narrow restricted neck and with a maximum volume space of 50 l, said electrical heating being a heating element consisting of a self-regulating strip heater secured in the interior of the container, and the supply line for said strip heater extending within and down said neck.

2. Device according to claim 1, said device comprising a casing fastened onto the neck of the container, and an on/off control switch and a fuse for supplying the current to said strip heater being mounted on said casing.

3. Device according to claim 2, said device comprising a time-control unit within said casing for prior selection of the duration of the therapy, and automatic switching-off of the device.

4. Device according to claim 3, said device comprising said strip heater being disposed at the bottom of said container.

* * * * *